United States Patent [19]
Mode

[11] Patent Number: 5,347,852
[45] Date of Patent: Sep. 20, 1994

[54] ON-LINE RHEOLOGICAL MEASUREMENTS FOR PROCESS CONTROL

[75] Inventor: Paul G. Mode, Westfield, N.J.

[73] Assignee: Rheometrics, Inc., Piscataway, N.J.

[21] Appl. No.: 29,792

[22] Filed: Mar. 11, 1993

[51] Int. Cl.$^5$ .................................. G01N 11/08
[52] U.S. Cl. ........................................... 73/54.04
[58] Field of Search ............... 73/54.04, 54.05, 54.06

[56] References Cited

U.S. PATENT DOCUMENTS

| | | | |
|---|---|---|---|
| 2,700,891 | 2/1955 | Shafer | 73/54.06 |
| 3,116,630 | 1/1964 | Piros | 73/54.04 |
| 3,465,573 | 9/1969 | Shoemaker | 73/54.01 |
| 3,559,464 | 2/1971 | Foust et al. | 73/54.06 |
| 3,977,235 | 8/1976 | Topham | 73/54.04 |
| 4,286,457 | 9/1981 | Johnson, Jr. | 73/54.09 |
| 4,442,704 | 4/1984 | Swearingen | 73/54.09 |
| 4,817,416 | 4/1989 | Blanch et al. | 73/54.04 |
| 4,932,242 | 6/1990 | Kawashima et al. | 73/54.07 |
| 4,992,487 | 2/1991 | Rao | 73/54.01 |
| 5,172,585 | 12/1992 | Gleissle | 73/54.04 |

FOREIGN PATENT DOCUMENTS

| | | | |
|---|---|---|---|
| 2398298 | 2/1979 | France | 73/54.04 |
| 155740 | 9/1984 | Japan | 73/54.06 |

OTHER PUBLICATIONS

T960,004 Nevile United States Defensive Publication, Jul. 5, 1977.
A. Goöttfert, Real time viscosity control with capillary rheumetry Göttfert Werkstuff-Prüfmaschinen GmbH, 1986.
On-Line Rheometer for Polymer melts bypass-Rheograph side Stream-Rheograph, Göttfert Werkstuff-Prüfmaschinen GmbH.

Primary Examiner—Hezron E. Williams
Assistant Examiner—Joseph W. Roskos
Attorney, Agent, or Firm—Samuelson & Jacob

[57] ABSTRACT

On-line rheological measurements are made utilizing a rheometer of the type in which a first metering pump delivers diverted melt from a process main stream to a capillary passage and a second metering pump returns the diverted melt from the capillary passage to the process main stream and the viscosity of the diverted melt is measured by controlling the rate of flow of the melt through the capillary passage to maintain constant the pressure drop between spaced apart locations along the capillary passage and measuring the temperature of the melt in the capillary passage. The measurements may be made while controlling the speed of the second metering pump independent of the speed of the first metering pump to maintain the pressure at the exit of the capillary passage essentially constant. A parallel flow passage has an inlet placed between the first metering pump and the entrance to the capillary passage, in close juxtaposition with the entrance and an outlet placed between the exit from the capillary passage and the second metering pump, and a valve in the parallel flow passage is operated so that diverted melt selectively is passed through the parallel flow passage to attain a relatively quick response and relatively short residence time of the diverted melt in the rheometer.

21 Claims, 6 Drawing Sheets

ON-LINE RHEOLOGICAL MEASUREMENTS FOR PROCESS CONTROL

The present invention relates generally to the measurement of rheological characteristics of melted materials and pertains, more specifically, to the on-line measurement of such characteristics as the viscosity of polymer melts for purposes of control of manufacturing processes involving molten plastics.

Rheological testing equipment has been available for a very long time in conducting laboratory measurements of certain important characteristics of polymer melts used in various manufacturing processes. Thus, such properties as viscosity and melt flow index are being measured in the laboratory with increasing accuracy. More recently, efforts have been directed toward the measurement of these characteristics on-line, during the manufacturing process itself, in order to provide constant, closer control over the quality of the melt utilized in the process. On-line measurement requires equipment which not only is relatively easy to use and maintain, but which is rugged enough to withstand the operating conditions to which the equipment will be exposed. In order to be effective, the equipment must be responsive, and must avoid disturbing the manufacturing process being monitored.

Among the more successful on-line rheometers available currently are capillary rheometers which divert a portion of the polymer melt from the main stream of molten plastic, conduct measurements on the diverted melt, and then either discard the diverted melt or return the diverted melt to the process main stream. In U.S. Pat. No. 4,817,416, the disclosure of which is incorporated herein by reference thereto, there is disclosed an on-line capillary rheometer and techniques for conducting on-line measurements of the type described above. The present invention constitutes an improvement in on-line capillary rheometers and in the techniques which utilize apparatus of the type in which melt is diverted to a rheometer and further extends the capability of such on-line rheometers to enable effective use in connection with the control of processes where measurements must be conducted quickly and response time must be held to a minimum, such as processes in which polymers are blended, alloyed or reacted. More specifically, the present invention has several objectives and provides a number of advantages, some of which are summarized as follows: Enables truly on-line measurements for attaining quicker response and more accurate control of manufacturing processes involving polymer melts; allows on-line measurements to be made in a polymer melt diverted from the process main stream with decreased residence time of the diverted polymer melt in the measuring apparatus, increased accuracy and quicker response; permits the conduct of on-line measurements with a minimal intrusion into the process being monitored; permits increased versatility in the nature and extent of the information derived from on-line measurements of polymer melts, as well as increased accuracy in the information itself; enables ease of installation and use in connection with current manufacturing equipment and techniques; allows ready adaptation for use in connection with a wide variety of materials and operating conditions; and provides a simple and rugged construction for economical manufacture and reliable long-term service.

The above objects and advantages, as well as further objects and advantages, are attained by the present invention, which may be described briefly as an improvement in apparatus and method for conducting an on-line rheological measurement in a process melt in a process main stream so as to provide process control information based upon the viscosity of the process melt, utilizing a rheometer of the type in which a first metering pump delivers diverted melt from a first conduit, communicating with the process main stream and the first metering pump, to an entrance of a capillary passage and a second metering pump delivers the diverted melt from an exit of the capillary passage to a second conduit communicating with the second metering pump, and measuring means for measuring the viscosity of the diverted melt in the capillary passage, the improvement comprising: providing a parallel passage having an inlet located between the first metering pump and the entrance the capillary passage, in close juxtaposition with the entrance, and an outlet located between the exit of the capillary passage and the second metering pump; and controlling the flow of diverted melt through the parallel passage alternately to enable a volumetric flow through the parallel passage at a rate which attains relatively quick delivery of diverted melt from the process main stream to the first metering pump, and to discontinue the volumetric flow through the parallel passage at said rate during measurement of the viscosity of the diverted melt in the capillary passage.

The invention will be understood more fully, while still further objects and advantages will become apparent, in the following detailed description of preferred embodiments of the invention illustrated in the accompanying drawing, in which.

Figure 1:
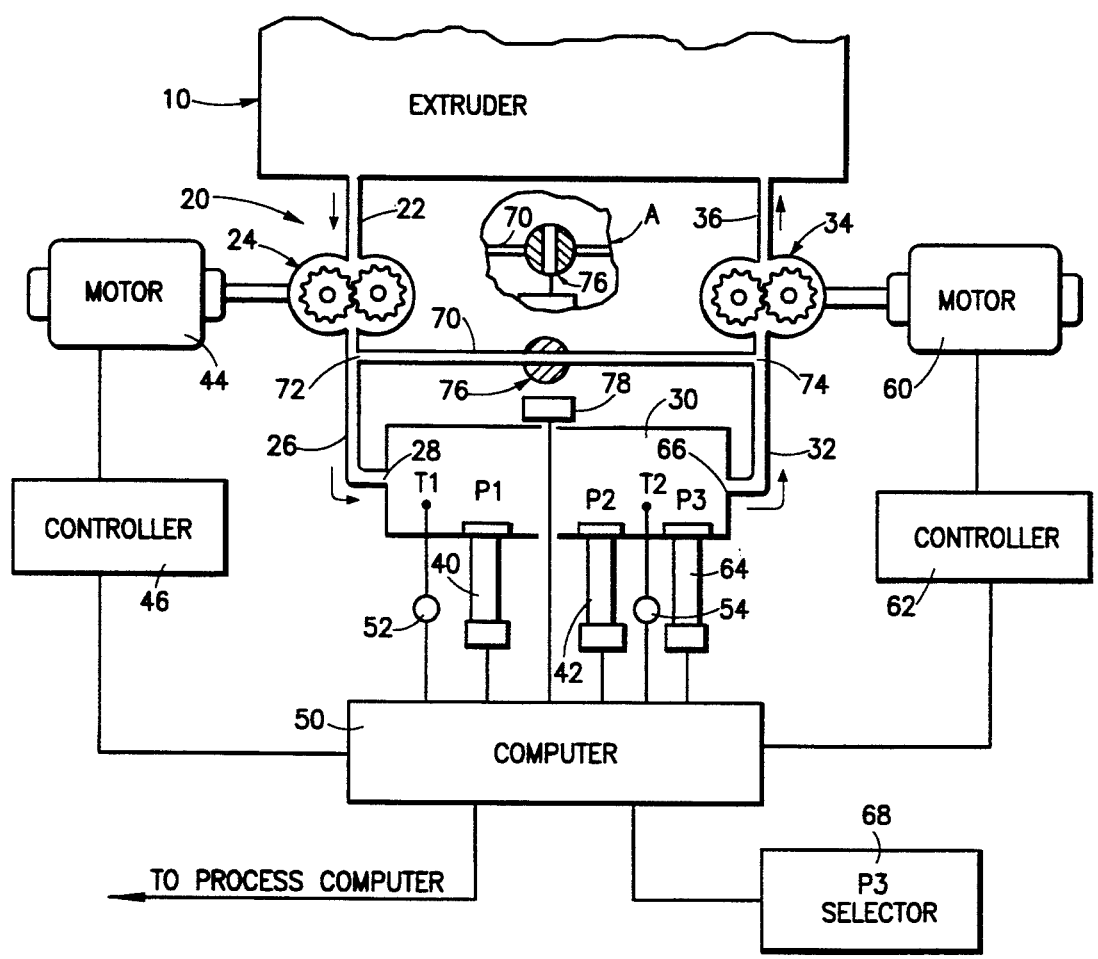
FIG. 1 is a schematic diagram of an on-line system employing the improvement of the present invention, and includes an inset A showing another operating position of a portion of the system.

Referring now to the drawing, and especially to FIG. 1 thereof, a plasticating extruder is shown schematically at 10. Extruder 10 is in use, generating melted polymer for the continuous manufacture of plastic material, such as plastic pellets. In order to assure that the quality of the extrudate meets the requirements of the manufacturing process, a control system is utilized in connection with the operation of the extruder 10 to monitor certain characteristics of the polymer melt and to operate the extruder in the manner necessary to attain the desired quality in the extrudate. An on-line rheometer 20, constructed in accordance with the present invention, is a part of that control system.

A portion of the polymer melt in the extruder 10 is diverted from the process main stream in the extruder to the rheometer 20 through an inlet conduit 22 and is advanced by a first metering pump 24 through an entrance conduit 26 to the entrance 28 to a capillary passage 30 of selected configuration and dimensions. The diverted polymer melt traverses the capillary passage 30 and then leaves the capillary passage 30 via an exit conduit 32. A second metering pump 34 advances the diverted polymer melt through an outlet conduit 36 which preferably communicates with the extruder 10 so that the diverted polymer melt is returned to the process main stream of polymer melt in the extruder 10. A first pressure-responsive transducer 40 is placed at a location adjacent the entrance 28 and provides information indicative of the pressure $P_1$ in the polymer melt at that location in the capillary passage 30. A second pressure-responsive transducer 42 is placed at a second location spaced downstream from the first location and provides information indicative of the pressure $P_2$ at the second location in the capillary passage 30. The rate of flow of the polymer melt in the capillary passage 30 is governed by the speed of the first metering pump 24 and that speed is determined by the speed of the motor 44 which drives the metering pump 24. The speed of motor 44 is controlled by a controller 46 which itself is connected to a computer 50. Temperature sensors 52 and 54 provide information to computer 50 indicative of the temperature ($T_1$ and $T_2$) of the polymer melt adjacent each of the locations of the pressure-responsive transducers 40 and 42.

As set forth in detail in the aforementioned U.S. Pat. No. 4,817,416, the pressure drop $P_1-P_2$ is maintained constant by controlling the speed of both the first and the second metering pumps 24 and 34. The speed of the first metering pump 24 then provides a measure of the rate of flow of the polymer melt traversing the capillary passage 30, which rate of flow is an indication of the viscosity of the polymer melt. Since the speed of the first metering pump 24 is known with precision, the viscosity is determined with a high degree of accuracy. Since the temperature dependence of polymer materials at constant stress is well known, the maintenance of a constant stress on the polymer melt in the capillary passage 30, that is, the maintenance of a constant pressure drop $P_1-P_2$, enables the temperature information, as determined by $T_1$ and $T_2$ (preferably by averaging $T_1$ and $T_2$), to be utilized to relate the measurements to a known standard so that it is not necessary to control the temperature of the diverted polymer melt, but merely to measure the temperature and then correct the measured viscosity information, in accordance with the measured temperature, to derive the desired control information. In this manner, viscosity measurements are enabled independent of the temperature of the diverted polymer melt. The information pertaining to pressure drop ($P_1-P_2$), rate of flow and temperature ($T_1$ and $T_2$) is directed to computer 50. Computer 50 then provides control information to a process computer which may be used in connection with the control of the operation of the extruder 10.

In order to maintain accuracy in the determination of viscosity, utilizing the above scheme, it is necessary to assure that the pressure drop ($P_1-P_2$) is solely a result of the traverse of the capillary passage 30 by the polymer melt, and that the measured pressures are not affected by any irregularities in the operation of the various components of the rheometer 20. As explained in U.S. Pat. No. 4,817,416, rheometer 20 includes means for driving the second metering pump 34 independent of the first metering pump 24, the means being illustrated in the form of a second motor 60 controlled by a second controller 62 connected to computer 50. A third pressure-responsive transducer 64 is located adjacent exit 66 from the capillary passage 30 and provides information indicative of the pressure $P_3$ at the exit. The information provided by the third pressure-responsive transducer 64 is utilized by the computer 50 to operate the controller 62 so that the motor 60 actuates the second metering pump 34 at the speed necessary to maintain the pressure $P_3$ constant. By maintaining the exit pressure $P_3$ constant, the pressure drop $P_1-P_2$ is related solely to the characteristics of the polymer melt traversing the capillary passage 30 and does not include any effects introduced by inaccuracies in the mechanical components of the rheometer 20. Hence, the information provided by computer 50 is related solely to the characteristics of the polymer melt for accurate control of the process being carried out in the extruder.

The operation of the second metering pump 34 independent of the first metering pump 24 enables the accomplishment of further significant measurements. Thus, in response to selected input into the computer 50, by means of a selector 68, the exit pressure $P_3$ can be changed to any selected constant pressure enabling the measurement of the viscosity of the polymer melt at different pressures, thereby enabling an evaluation of the response of viscosity to pressure. These measurements provide additional information enabling enhanced control of the quality of the extrudate produced by the extruder 10.

In order to reduce residence time and decrease response time, thereby enabling even more truly on-line operation, a parallel flow passage 70 has an inlet 72 placed between the first metering pump 24 and the entrance 28 to the capillary passage 30, in close juxtaposition with the entrance 28, and an outlet 74 placed between the exit 66 of the capillary passage 30 and the second metering pump 34, preferably closely adjacent the exit 66. Control means include valve means shown in the form of a rotary valve 76 placed in the parallel flow passage 70 for controlling the flow of diverted melt through the parallel flow passage 70. The volumetric flow capacity of the parallel flow passage 70 preferably is greater than the volumetric flow capacity of the capillary passage 30, as is the predetermined volumetric flow capacity of the inlet conduit 22 and the predetermined volumetric flow capacity of the outlet conduit 36. Thus, upon opening the valve 76, as depicted in the full diagram of FIG. 1, by means of a valve controller 78 operated by computer 50, to enable the flow of diverted melt through the parallel flow passage 70, and upon increasing the speed of operation of the metering pumps 24 and 34, fresh melt very quickly is delivered from the extruder 10 to the entrance 28 of the capillary passage 30 for the desired measurement. Upon closing the valve 76, as shown in inset A of FIG. 1, flow of the diverted melt through the parallel passage 70 is discontinued and the speed of each metering pump 24 and 34 is controlled to attain the desired measurement, as set forth above. Upon completion of the measurement, the valve 76 is opened again and the metering pumps 24 and 34 are operated to return the diverted melt to the process main stream, through the outlet conduit 36, and to draw fresh diverted melt from the process main stream, through the inlet conduit 22. In this manner, a fresh supply of diverted melt is moved quickly from the extruder 10 to the capillary passage 30 at a rate of flow which is not limited to the volumetric flow capacity of the capillary passage 30, and diverted melt is made available for measurement more rapidly for quicker response. In addition, since the volumetric flow capacities of the inlet conduit 22 and of the outlet conduit 36 now are independent of the volumetric flow capacity of the capillary passage 30, this quick response is attained even with longer length inlet and outlet conduits 22 and 36. Moreover, the rapid response and decreased residence time is accomplished utilizing only the metering pumps 24 and 36, without the necessity for any additional pump and pump controller. All that need be added to the existing apparatus, as described in U.S. Pat. No. 4,817,416, is the parallel flow passage 70, valve 76 and valve controller 78, thereby reducing bulk, complexity and expense.

In the preferred embodiment, the volumetric flow capacity of the parallel flow passage 70 is at least about four times greater than the volumetric flow capacity of capillary passage 30. The predetermined volumetric flow capacity of the inlet conduit 22 and of the outlet conduit 36 is such that the metering pumps 24 and 34 can be operated by computer 50, through controllers 46 and 62, respectively, to very quickly move a fresh supply of diverted melt to the capillary passage 30 for more truly on-line measurements. In addition, the placement of the parallel flow passage 70 between the metering pumps 24 and 34 and the capillary passage 30 and the use of metering pumps 24 and 34, as described, assures that the capillary passage 30 will not be starved during the measuring procedure.

Figure 2:
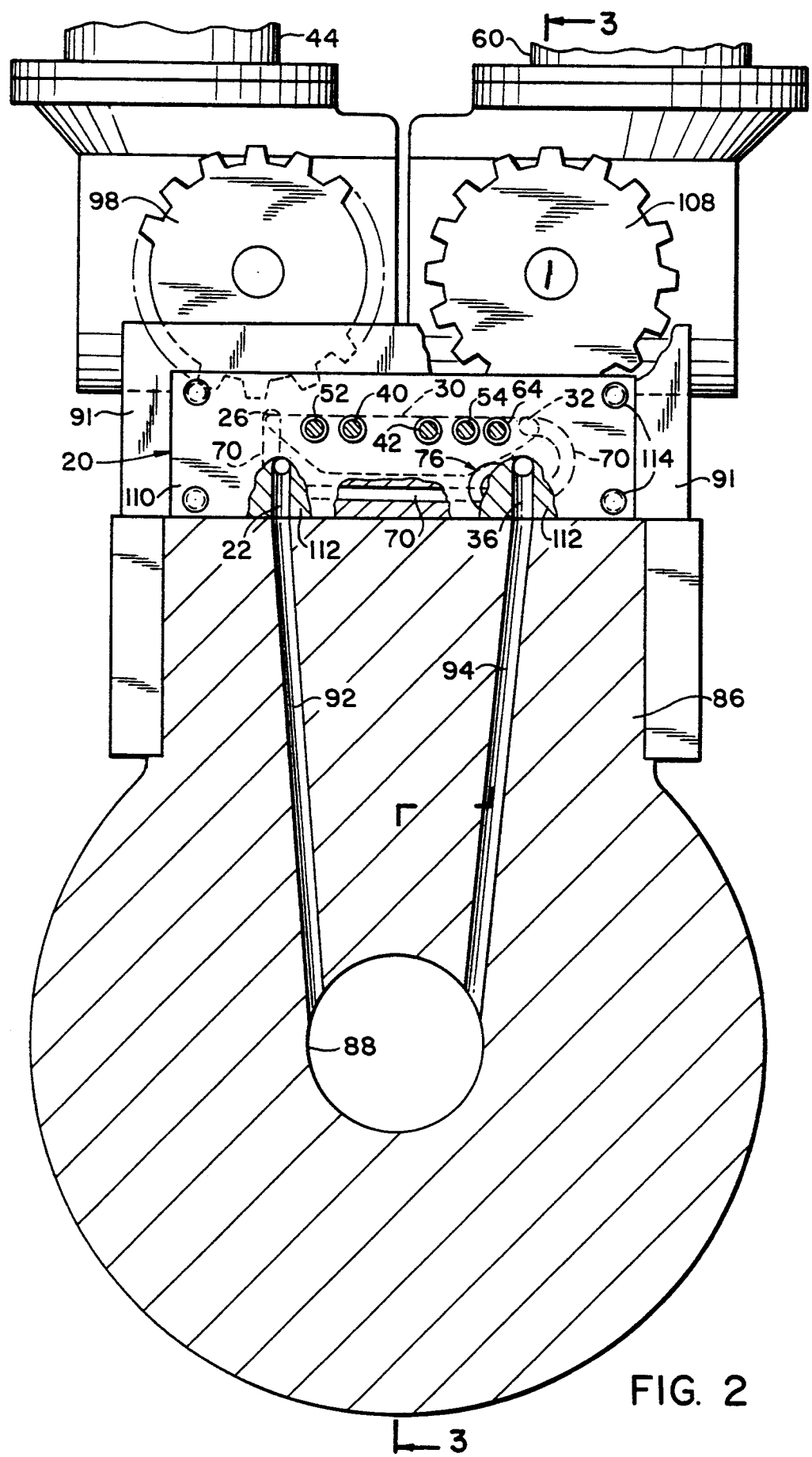
FIG. 2 is a transverse cross-sectional view of an apparatus constructed in accordance with the invention installed in a plasticating extruder.
Figure 3:
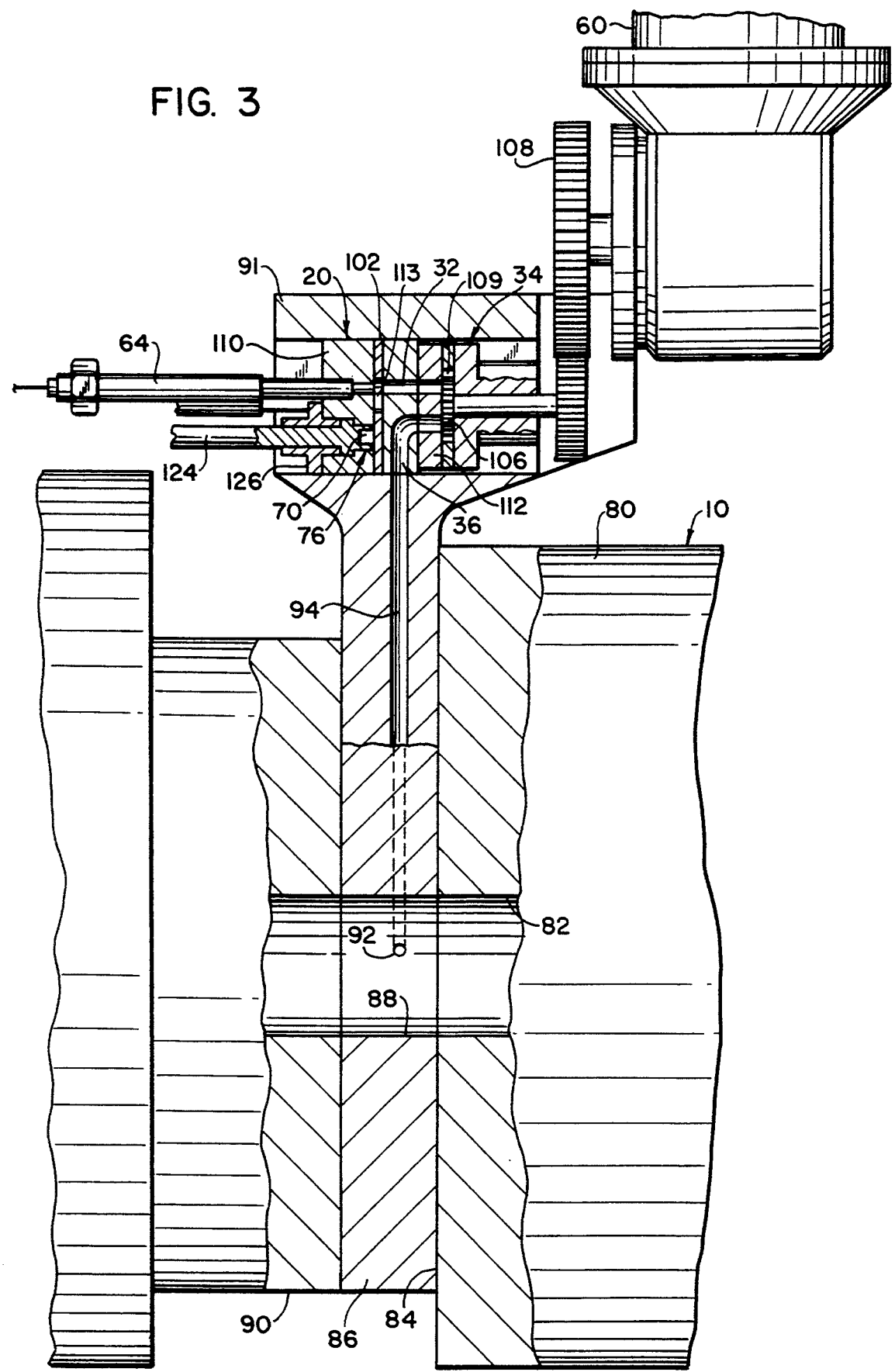
FIG. 3 is a cross-sectional view taken along line 3—3 of FIG. 2.

Turning now to FIGS. 2 and 3, there is illustrated a typical installation in which a rheometer 20 is mounted upon an extruder 10 for on-line operation. Extruder 10 has a barrel 80 which includes an outlet bore 82 at the output end 84 of the extruder 10. A mounting plate 86 is affixed to the end 84 of the barrel 80 and has an aperture 88 which matches the outlet bore 82 of the extruder 10. A further orifice plate 90 is placed downstream of the mounting plate 86. Rheometer 20 is secured to the mounting plate 86 by means of a bracket 91 which is integral with the mounting plate 86 so as to be in very close proximity to the main stream of polymer melt passing from the extruder 10, through the outlet bore 82. An inlet passage 92 in the mounting plate 86 communicates with the aperture 88 and provides a conduit to the inlet conduit 22 of the rheometer 20. An outlet passage 94 in the mounting plate 86 also communicates with the aperture 88 and provides a conduit from the outlet conduit 36 of the rheometer 20 back to the aperture 88. A portion of the polymer melt is diverted from the process main stream in the outlet bore 82 and the aperture 88 to the inlet passage 92 and is conducted to the inlet conduit 22 of the rheometer 20. The first metering pump 24 is in the form of a gear pump having a pair of gear-type impellers 96 (see FIG. 4) coupled to the first motor 44 through a drive train 98 for rotation in a pump chamber 99. Capillary passage 30 is in the form of a slot 100 in a capillary plate 102 and the pump chamber 99 communicates with the slot 100 through entrance conduit 26 to deliver the diverted polymer melt from the inlet conduit 22 to the capillary passage 30. Thus, first metering pump 24 is in very close proximity to the entrance 28 of the capillary passage 30. The diverted polymer melt traverses the capillary passage 30 and is delivered to the second metering pump 34 via the exit conduit 32. Second metering pump 34 also is in the form of a gear pump having a pair of gear-type impellers 106 coupled to the second motor 60 through a drive train 108 for rotation in a pump chamber 109, independent of the rotation of the impellers 96 of the first metering pump 24. The outlet conduit 36 communicates with the pump chamber 109 and enables return of the diverted polymer melt to the process main stream in the aperture 88. Thus, second metering pump 34 is in very close proximity to the exit 66 of capillary passage 30.

Figure 4:
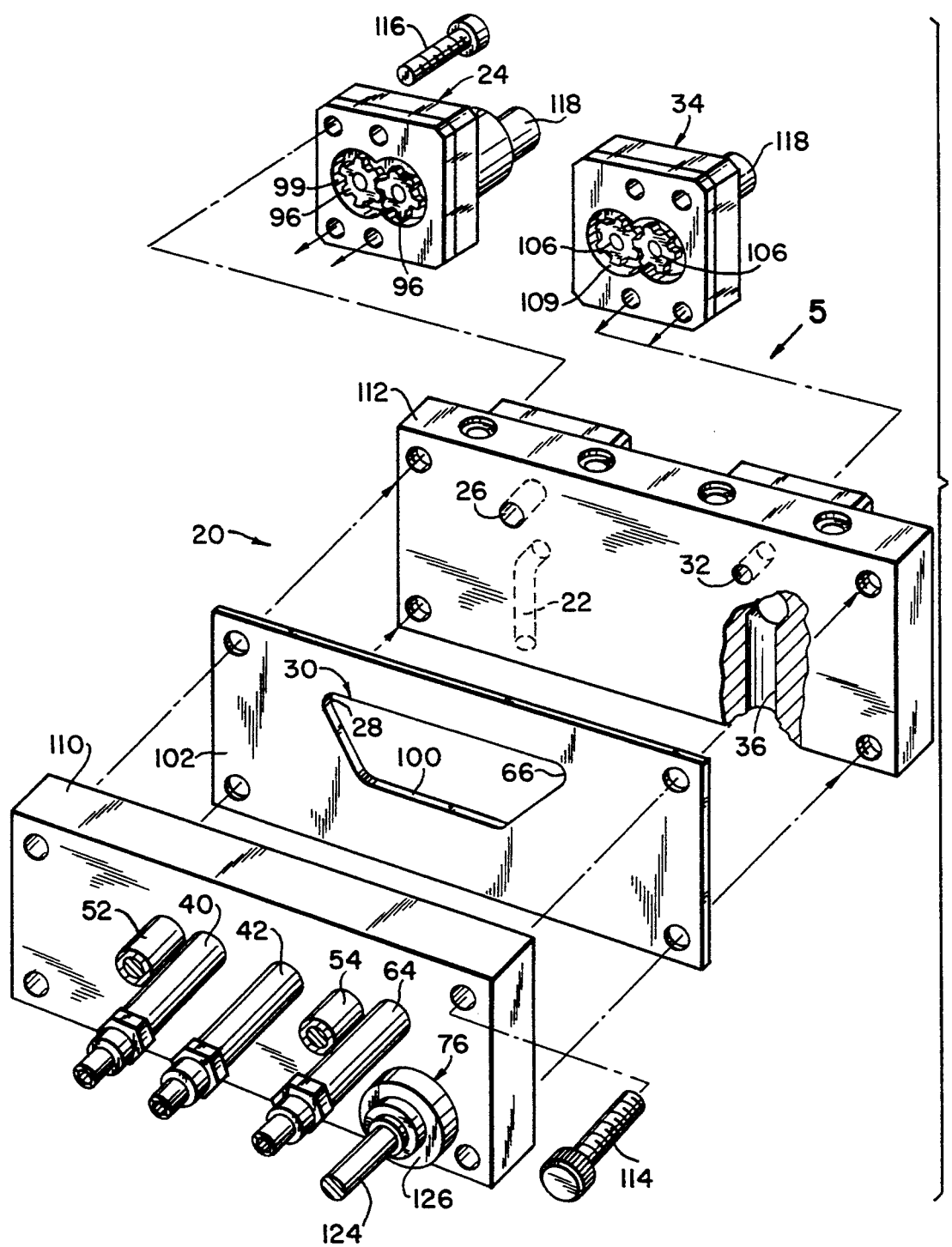
FIG. 4 is an exploded perspective view of portions of the apparatus.
Figure 5:
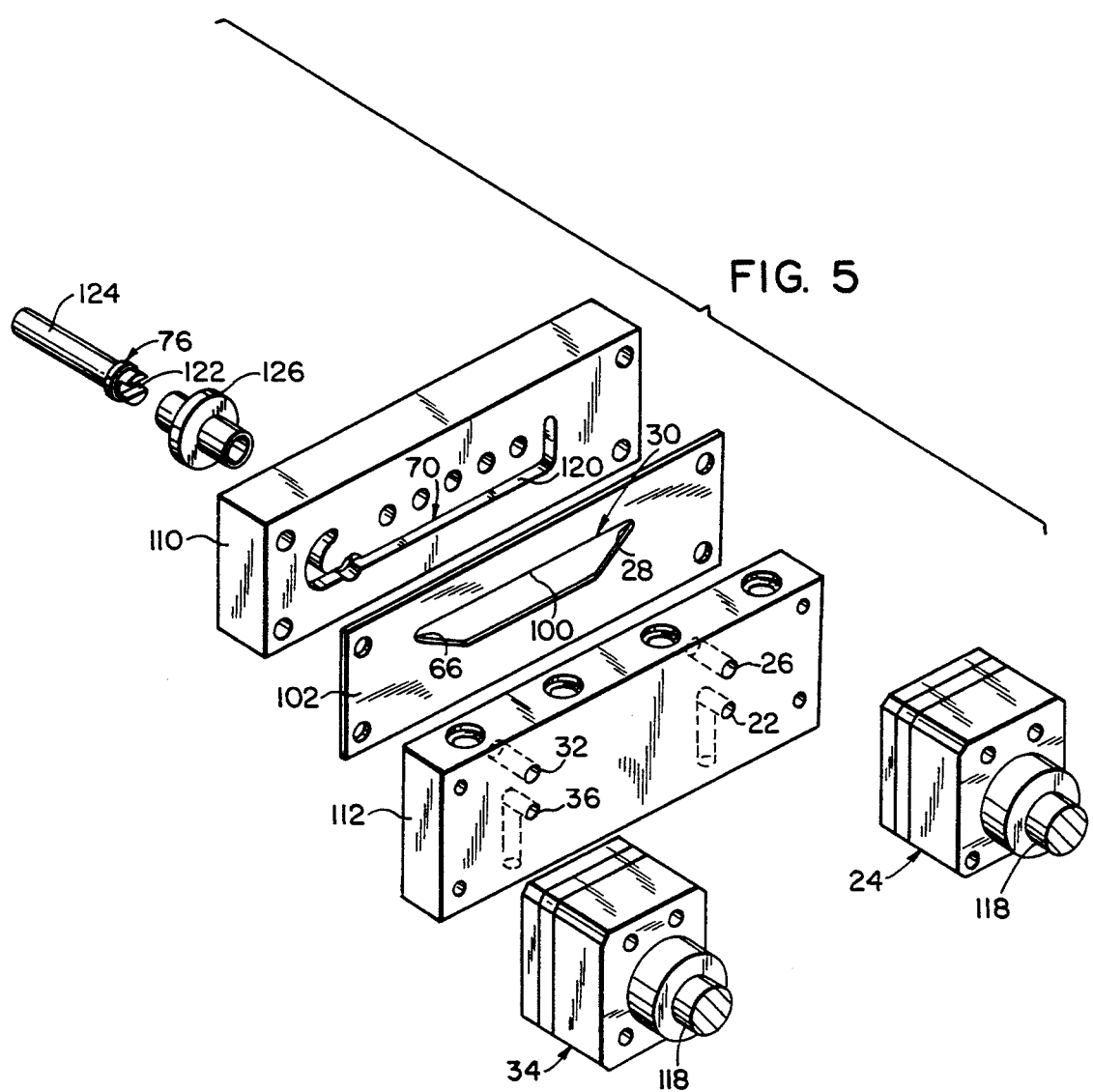
FIG. 5 is an exploded perspective view similar to FIG. 4 but taken in the direction of the arrow in FIG. 4.

As best seen in FIGS. 4 and 5, as well as in FIGS. 2 and 3, rheometer 20 preferably is constructed of assembled component parts which include a first block 110 and a second block 112 between which blocks 110 and 112 is interposed the capillary plate 102 such that the slot 100, when placed between the blocks 110 and 112, establishes a chamber 113 (see FIG. 3) which provides the capillary passage 30. The blocks 110 and 112 and the capillary plate 102 are secured together, as with threaded fasteners 114, to establish an integral unit which may be dismantled at will. The metering pumps 24 and 34 likewise are secured to the second block 112, in close proximity to the capillary passage 30, by means of threaded fasteners 116, each metering pump having a drive shaft 118 for coupling the impellers of the pump to the respective drive train. The second block 112 also includes the inlet conduit 22, the entrance conduit 26, the exit conduit 32 and the outlet conduit 36. The first block 110 carries the pressure-responsive transducers 40, 42 and 64, and the temperature sensors 52 and 54.

The parallel flow passage 70 is in the form of a groove 120 in the first block 110, the groove 120 communicating with the entrance conduit 26 at inlet 72, so as to be closely juxtaposed with entrance 28 of capillary passage 30, and with the exit conduit 32 at outlet 74, closely adjacent exit 66. Valve 76 includes a valve passage 122 in a valve stem 124, and the valve stem 124 is journaled for rotation in a valve bushing 126 secured to the first block 100. Valve controller 78 (see FIG. 1) is coupled to the valve stem 124 for rotating the valve stem 124 through angular displacements between an open position, as seen in the full diagram of FIG. 1, and a closed position, as seen in inset A of FIG. 1.

The capillary plate 102 is relatively thin and the configuration and dimensions of the capillary slot 100 are chosen to provide a capillary passage 30 of corresponding configuration and dimensions appropriate for enabling the desired measurements to be made in the particular polymer involved in the process being monitored. The various conduits in the second block 112 and the several transducers and sensors in the first block 110 are placed so as to be located appropriately relative to the slot 100. The groove 120 has a cross-sectional area large enough to provide the parallel flow passage 70 with a volumetric flow capacity greater than the volumetric flow capacity of capillary passage 30. In the preferred arrangement, the volumetric flow capacity of the parallel flow passage 70 is at least about four times greater than the volumetric flow capacity of capillary passage 30.

Figure 6:
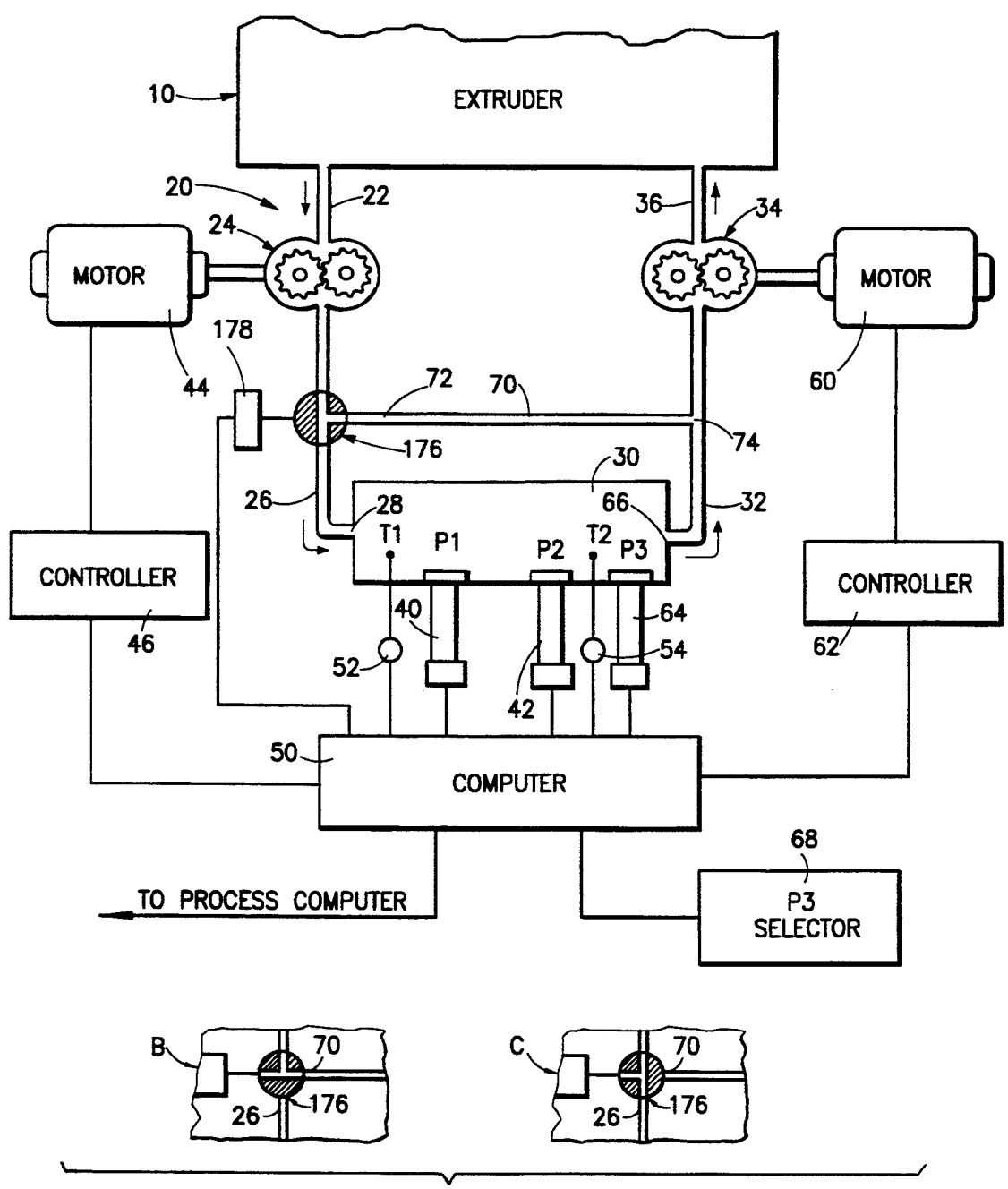
FIG. 6 is a schematic diagram similar to FIG. 1, illustrating an on-line system employing an alternate embodiment of the improvement of the present invention, and includes insets B and C showing other operating positions of a portion of the system.

Turning now to the embodiment of FIG. 6, the valve 76 and valve controller 78 have been replaced by a valve 176 and valve controller 178 which controls the rotation of valve 176 through angular displacements to the positions illustrated in the full diagram of FIG. 6 and in the insets B and C. In the position of valve 176 illustrated in the full diagram, flow of the diverted melt is permitted through both the capillary passage 30 and the parallel flow passage 70, and diverted melt previously delivered to the capillary passage 30 and to the parallel flow passage 70 is purged from both the capillary passage 30 and the parallel flow passage 70. In the position of valve 176 shown in inset B, the flow of diverted melt to the capillary passage 30 is discontinued, while the flow of diverted material through the parallel flow passage 70 enables fresh diverted melt to be delivered rapidly toward the entrance conduit 26 and entrance 28 of capillary passage 30. In the position of the valve 176 shown in inset C, the flow of diverted melt to the parallel flow passage 70 is discontinued and the fresh diverted melt is routed to the capillary passage 30 for the conduct of measurements, as described above.

It will be seen that the above-described apparatus and procedure enables truly on-line measurements for quicker response and more accurate control of manufacturing processes involving polymer melts; allows on-line measurements to be made in a polymer melt diverted from the process main stream with decreased residence time of the diverted polymer melt in the measuring apparatus, increased accuracy and quicker response; permits the conduct of on-line measurements with a minimal intrusion into the process being monitored; permits increased versatility in the nature and extent of the information derived from on-line measurements of polymer melts, as well as increased accuracy in the information itself; enables ease of installation and use in connection with current manufacturing equipment and techniques; allows ready adaptation for use in connection with a wide variety of materials and operating conditions; and provides a simple and rugged construction for economical manufacture and reliable long-term service.

It is to be understood that the above detailed description of embodiments of the invention is provided by way of example only. Various details of design, construction and procedure may be modified without departing from the true spirit and scope of the invention as set forth in the appended claims.

The embodiments of the invention in which an exclusive property or privilege is claimed are defined as follows:

1. An improvement in an apparatus for conducting an on-line rheological measurement in a process melt in a process main stream so as to provide process control information based upon the viscosity of the process melt, utilizing a rheometer of the type in which a first metering pump delivers diverted melt from a first conduit, communicating with the process main stream and the first metering pump, to an entrance of a capillary passage and a second metering pump delivers the diverted melt from an exit of the capillary passage to a second conduit communicating with the second metering pump, and measuring means for measuring the viscosity of the diverted melt in the capillary passage, the improvement comprising:

a parallel flow passage having an inlet located between the first metering pump and the entrance to the capillary passage, in close juxtaposition with the entrance, and an outlet located between the exit of the capillary passage and the second metering pump; and control means for controlling the flow of diverted melt through the parallel flow passage alternately to enable a volumetric flow through the parallel flow passage at a rate which attains relatively quick delivery of diverted melt from the process main stream to the first metering pump, and to discontinue the volumetric flow through the parallel flow passage at said rate during measurement of the viscosity of the diverted melt in the capillary passage.

2. The invention of claim 1 wherein the control means includes valve means for discontinuing the flow of diverted melt through the parallel flow passage during measurement of the viscosity of the diverted melt in the capillary passage.

3. The invention of claim 1 wherein the control means includes valve means for discontinuing the flow of diverted melt through the capillary passage when the volumetric flow through the parallel flow passage is at said rate.

4. The invention of claim 1 wherein the first conduit has a predetermined volumetric flow capacity, the capillary passage has a volumetric flow capacity lower than the predetermined flow capacity of the first conduit, and the parallel flow passage has a volumetric flow capacity higher than the flow capacity of the capillary passage.

5. The invention of claim 4 wherein the volumetric flow capacity of the parallel flow passage is at least about four times the volumetric flow capacity of the capillary passage.

6. The invention of claim 4 wherein the control means includes valve means for discontinuing the flow of diverted melt through the parallel flow passage during measurement of the viscosity of the diverted melt in the capillary passage.

7. The invention of claim 6 wherein the volumetric flow capacity of the parallel flow passage is at least about four times the volumetric flow capacity of the capillary passage.

8. The invention of claim 4 wherein the control means includes valve means for discontinuing the flow of diverted melt through the capillary passage when the volumetric flow through the parallel flow passage is at said rate.

9. The invention of claim 1 wherein the second conduit communicates with the process main stream such that the diverted melt is returned by the second metering pump to the process main stream.

10. The invention of claim 9 wherein the control means includes valve means for discontinuing the flow of diverted melt through the parallel flow passage during measurement of the viscosity of the diverted melt in the capillary passage.

11. The invention of claim 9 wherein the control means includes valve means for discontinuing the flow of diverted melt through the capillary passage when the volumetric flow through the parallel flow passage is at said rate.

12. The invention of claim 9 wherein the first conduit has a predetermined volumetric flow capacity, the capillary passage has a volumetric flow capacity lower than the predetermined flow capacity of the first conduit, and the parallel flow passage has a volumetric flow capacity higher than the flow capacity of the capillary passage.

13. The invention of claim 12 wherein the volumetric flow capacity of the parallel flow passage is at least about four times the volumetric flow capacity of the capillary passage.

14. The invention of claim 12 wherein the control means includes valve means for discontinuing the flow of diverted melt through the parallel flow passage during measurement of the viscosity of the diverted melt in the capillary passage.

15. The invention of claim 12 wherein the control means includes valve means for discontinuing the flow of diverted melt through the capillary passage when the volumetric flow through the parallel flow passage is at said rate.

16. The invention of claim 15 wherein the volumetric flow capacity of the parallel flow passage is at least about four times the volumetric flow capacity of the capillary passage.

17. An improvement in a method for conducting an on-line rheological measurement in a process melt in a process main stream so as to provide process control information based upon the viscosity of the process melt, utilizing a rheometer of the type in which a first metering pump delivers diverted melt from a first conduit, communicating with the process main stream and the first metering pump, to an entrance of a capillary passage and a second metering pump delivers the diverted melt from an exit of the capillary passage to a second conduit communicating with the second metering pump, and measuring means for measuring the viscosity of the diverted melt in the capillary passage, the improvement comprising:

providing a parallel flow passage having an inlet located between the first metering pump and the entrance to the capillary passage, in close juxtaposition with the entrance, and an outlet located between an exit of the capillary passage and the second metering pump; and controlling the flow of diverted melt through the parallel flow passage alternately to enable a volumetric flow through the parallel flow passage at a rate which attains relatively quick delivery of diverted melt from the process main stream to the first metering pump, and to discontinue the volumetric flow through the parallel flow passage at said rate during measurement of the viscosity of the diverted melt in the capillary passage.

18. The invention of claim 17 wherein controlling the flow of diverted melt through the parallel flow passage includes discontinuing the flow of diverted melt through the parallel flow passage during measurement of the viscosity of the diverted melt in the capillary passage.

19. The invention of claim 17 including discontinuing the flow of diverted melt through the capillary passage when the volumetric flow through the parallel flow passage is at said rate.

20. The invention of claim 17 including returning the diverted melt from the second metering pump to the process main stream.

21. The invention of claim 17 wherein said rate of volumetric flow through the parallel flow passage is at least about four times the volumetric flow capacity of the capillary passage.

* * * * *